United States Patent [19]

Wood et al.

[11] 4,342,834

[45] * Aug. 3, 1982

[54] ENZYMES BOUND TO POLYURETHANE

[75] Inventors: Louis L. Wood, Rockville; Frank J. Hartdegen; Peter A. Hahn, both of Columbia, all of Md.

[73] Assignee: W. R. Grace & Co., New York, N.Y.

[*] Notice: The portion of the term of this patent subsequent to Jan. 26, 1999, has been disclaimed.

[21] Appl. No.: 685,230

[22] Filed: May 11, 1976

Related U.S. Application Data

[60] Continuation of Ser. No. 574,778, May 5, 1975, abandoned, which is a division of Ser. No. 362,488, May 21, 1973, Pat. No. 4,312,946, which is a continuation-in-part of Ser. No. 250,012, May 3, 1972, abandoned.

[51] Int. Cl.³ .................... C12N 11/08; C12N 11/04
[52] U.S. Cl. .................................... 435/182; 435/180
[58] Field of Search ................. 195/63, 68, DIG. 11; 435/180, 182

[56] References Cited

U.S. PATENT DOCUMENTS

| | | | |
|---|---|---|---|
| 3,574,062 | 4/1971 | Sato | 195/63 |
| 3,672,955 | 6/1972 | Stanley | 195/68 |
| 3,705,084 | 12/1972 | Reynolds | 195/63 |
| 3,791,927 | 2/1974 | Forgione et al. | 195/63 |

*Primary Examiner*—Lionel M. Shapiro
*Attorney, Agent, or Firm*—Philip M. Pippenger

[57] ABSTRACT

To chemically bind either impure or purified enzymes to polyurethane to produce insolubilized bound enzymes which are still enzymically active and which may be more stable than the original enzyme, and which can be reused without appreciable activity loss and whose physical characteristics can be varied depending on the application for which they are intended.

3 Claims, No Drawings

ENZYMES BOUND TO POLYURETHANE

CROSS REFERENCE TO RELATED APPLICATION

This is a continuation of application Ser. No. 574,778, filed May 5, 1975, and now abandoned; said application Ser. No. 574,778 is a divisional of application Ser. No. 362,488 filed May 21, 1973, and now U.S. Pat. No. 4,312,946 issued Jan. 26, 1982; said application Ser. No. 362,488 is a continuation-in-part of application Ser. No. 250,012, filed May 3, 1972 and now abandoned. Application Ser. No. 404,823, filed Oct. 9, 1973, and now abandoned, is also a continuation-in-part of said application Ser. No. 250,012.

This invention is directed to a process for binding enzymes in active and reusable form on a polyurethane foam and to the resulting product. The polyurethane is produced in the known way by the reaction of di- and tri-isocyanates and other polyisocyanates with compounds containing active hydrogen, particularly glycols, polyglycols, polyester polyols and polyether polyols. This reaction makes an isocyanate-capped polyurethane. The enzyme preferably in aqueous media is bound by bringing it into contact with the polyurethane before the polyurethane is foamed. Since the polymerization reaction (e.g. of the polyol with the isocyanate) is exothermic, the temperature of the reaction mixture is maintained at below the temperature of thermal denaturation for the enzyme. In the binding step, the enzyme is maintained in a native conformation by the use of proper pH, ionic strength, presence of substrate, or necessary cations. The bound enzyme so produced is catalytically active.

The binding reaction is a general one applicable to substantially all enzymes. For example, the following are suitable: urease, cellulase, pectinase, papain, bromelain, chymotrypsin, trypsin, ficin, lysozyme, glucose isomerase, lactase, and penicillin amidase. We have found no enzyme which does not work. The form of the enzyme is not critical. Binding has been done using pure crystalline enzymes (lysozyme, trypsin); with partially purified non-crystalline enzymes (papain, bromelain); with impure extracts containing enzyme activity (ficin, pectinase); with unseparated fermentation broths containing an extracellular enzyme without purification or concentration (cellulase) and with intracellular enzymes bound to the cell walls (glucose isomerase). Our work indicates that our invention can be used to bind enzymes of substantially any purity.

We are aware of U.S. Pat. No. 3,672,955, to Stanley. In that patent enzymes are bound to isocyanate-capped polyurethanes. However, the binding process precludes formation of a foam. In the process of this patent the isocyanate-capped polyurethane is dissolved in a water-immiscible solvent. This solution is emulsified, using an emulsifying agent in the presence of an active enzyme. The enzyme is dispersed in water, and although the water reacts with the isocyanate groups to form bubbles or carbon dioxide, this gas is immediately released because of the very low viscosity of the solution, which in turn is caused by the use of the water-immiscible solvent. In the process of our invention these gas bubbles are retained, and the reason that they are retained is that no water-immiscible solvent is present to reduce the viscosity of the polyurethane solution. The fact that we get a foam, whereas the prior art as represented by U.S. Pat. No. 3,672,955 got a solid polyurethane, results in a considerable improvement. Firstly, the amount of enzyme retained in the isocyanate-capped polyurethane is greatly increased. Secondly, the conversion of product being treated with the bound enzyme is increased. Thirdly, a foam polyurethane product having inherently high surface area and great structural strength is much more convenient to use from the technical viewpoint than the product of U.S. Pat. No. 3,672,955 (i.e., a polyurethane dispersed on a carrier such as rice hulls, etc.)

Our process is similar in some respects to that of U.S. Pat. No. 3,672,955. We use the same isocyanate-capped polyurethanes (which that patent refers to as polyisocyanates); we use the same polyols; and we use the same enzymes. As in that patent (although we do not wish to be bound to any particular theory) the mechanism is apparently the reaction of one or more amino groups on the enzyme with one or more isocyanate groups on the polyurethane molecule. Hence, as in that patent, we require an excess of isocyanate groups on the polyurethane molecule. This is always readily attained by the use of a stoichiometric excess of isocyanate compound over the hydroxyl containing reactant. Such excess will insure that the polyurethane molecule contains unreacted isocyanate groups. However, since we do not use a water-immiscible solvent, we are able to get a foam. (In fact we aim deliberately at getting a foam.) As we shall show, the use of a foamed polyurethane gives a great and unobvious improvement in results, as compared to not using a foam.

Any polyurethane which contains at least two free isocyanate groups per polyurethane molecule is suitable for binding enzymes in accordance with this invention. We prefer that the polyurethane contain an average of two isocyanate groups per molecule. An even higher ratio can be used, for example, 2-8 isocyanate groups per polyurethane molecule. Ratios higher than this are operable, but offer no advantage. In any case, all excess isocyanate groups left in the polyurethane foam (after binding of the enzyme) will be destroyed by hydrolysis upon the first contact of the foam with water, for example, during the washing step preliminary to use of the bound enzyme.

As used herein, "isocyanate-capped polyurethane" means a polyurethane or polyurea molecule containing at least one free isocyanate group.

Representative examples of polyisocyanates which can be reacted with an active hydrogen containing compound (e.g., a glycol, polyol, polyglycol, polyester polyol, polyether polyol and the like) to make an isocyanate-capped polyurethane in accordance with the invention include:

toluene-2,4-diisocyanate
toluene-2,6-diisocyanate
commercial mixtures of toluene-2,4- and 2,6-diisocyanates
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
3,3'-dichloro-4,4'-biphenylene diisocyanate
1,6-hexamethylenediisocyanate
1,4-tetramethylene-diisocyanate 1,10-decamethylenediisocyanate
1,5-naphthalenediisocyanate
cumene-2,4-diisocyanate
4-methoxy-1,3-phenylenediisocyanate
4-chloro-1,3-phenylenediisocyanate
4-bromo-1,3-phenylenediisocyanate
4-ethoxy-1,3-phenylenediisocyanate
2,4'-diisocyanatodiphenylether
5,6-dimethyl-1,3-phenylenediisocyanate
2,4-dimethyl-1,3-phenylenediisocyanate
4,4'-diisocyanatodiphenylether
benzidinediisocyanate
4,6-dimethyl-1,3-phenylenediisocyanate
9,10-anthracenediisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethyl-4,4'-diisocyanatodiphenyl
3,3'-dimethoxy-4,4'-diisocyanatodiphenyl
1,4-anthracenediisocyanate
2,5-fluorenediisocyanate
1,8-naphthalenediisocyanate
2,6-diisocyanatobenzfuran
2,4,6-toluenetriisocyanate, and
p,p',p"-triphenylmethane triisocyanate.

A useful class of isocyanate-capped polyurethanes are those derived from polyether polyols and polyester polyols. These compounds may be prepared, as well known in the art, by reacting a polyether (or polyester) polyol with a polyisocyanate, using an excess of the latter to ensure provision of free isocyanate groups in the product. A typical, but by no means limiting, example is illustrated in idealized equation form below:

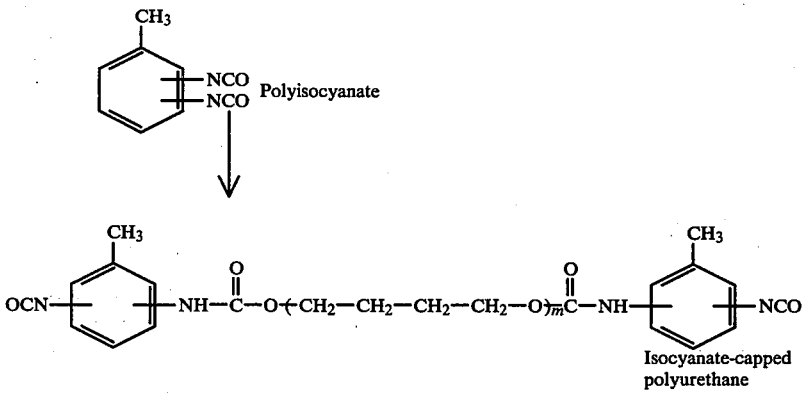

(In the above formulas, m represents the number of tetramethyleneether repeating units. This may range, for example, about from 5 to 50).

The compounds useful for the purposes of the invention may be prepared by reacting any of the above-exemplified polyisocyanate with any of a wide variety of polyether polyols and polyester polyols, and representative examples of these polyols are described below.

Among the polyether polyols which may be so used are those prepared by reaction of an alkylene oxide with an initiator containing active hydrogen groups, a typical example of the initiator being a polyhydric alcohol such as ethylene glycol; a polyamine such as ethylene diamine; phosphoric acid, etc. The reaction is usually carried out in the presence of either an acidic or basic catalyst. Examples of alkylene oxides which may be employed in the synthesis include ethylene oxide, propylene oxide, any of the isomeric butylene oxides, and mixtures of two or more different alkylene oxides such as mixtures of ethylene and propylene oxides. The resulting polymers contain a polyether backbone and are terminated by hydroxyl groups. The number of hydroxyl groups per polymer molecule is determined by the functionality of the active hydrogen initiator. For example, a difunctional alcohol such as ethylene glycol (as the active hydrogen initiator) leads to polyether chains in which there are two hydroxyl groups per polymer molecule. When polymerization of the oxide is carried out in the presence of glycol, a trifunctional alcohol, the resulting polyether molecules contain an average of three hydroxyl groups per molecule. Even higher functionality—more hydroxyl groups—is obtained when the oxide is polymerized in the presence of such polyols as pentaerythritol, sorbitol, sucrose diphentaerythritol, and the like. In addition to those listed above, other examples of polyhydric alcohols which may be reacted with alkylene oxides to produce useful polyether polyols include:

propylene glycol
trimethylene glycol
1,2-butylene glycol
1,3-butanediol
1,4-butanediol
1,5-pentanediol
1,2-hexylene glycol
1,10-decanediol
1,2-cyclohexanediol
2-butene-1,4-diol 3-cyclohexene-1,1-dimethanol
4-methyl-3-cyclohexene-1,1-dimethanol
3-methylene-1,5-pentanediol
diethylene glycol
(2-hydroxyethoxy)-1-propanol
4-(2-hydroxyethoxy)-1-butanol
5-(2-hydroxypropoxy)-1-pentanol
1-(2-hydroxymethoxy)-2-hexanol
1-(2-hydroxypropoxy)-2-octanol
3-allyloxy-1,5-pentanediol
2-allyloxymethyl-2-methyl-1,3-propanediol
[(4-pentyloxy)methyl]-1,3-propanediol
3-(o-propenylphenoxy)-1,2-propane diol thiodiglycol 2,2'-[thiobis(ethyleneoxy)]diethanol
polyethyleneether glycol (molecular weight about 200)
2,2'-isopropylidenebis(p-phenyleneoxy)diethanol
1,2,6-hexanetriol
1,1,1-trimethylolpropane
3-(2-hydroxyethoxy)-1,2-propanediol
3-(2-hydroxypropoxy)-1,2-propanediol
2,4-dimethyl-2-(2-hydroxyethoxy)methylpentanediol-1,5
1,1,1-tris[(2-hydroxyethoxy)methyl]ethane
1,1,1-tris[(2-hydroxypropoxy)methyl]propane
triethanolamine
triisopropanolamine
resorcinol
pyrogallol
phloroglucinol
hydroquinone
4,6-di-tertiarybutyl catechol
catechol
orcinol
methylphloroglucinol
hexylresorcinol
3-hydroxy-2-naphthol
2-hydroxy-1-naphthol
2,5-dihydroxy-1-naphthol
bis-phenols such as 2,2-bis(p-hydroxyphenyl)propane and bis-(p-hydroxyphenyl)methane
1,1,2-tris-(hydroxyphenyl)ethane
1,1,3-tris-(hydroxyphenyl)propane.

An especially useful category of polyether polyols are the polytetramethylene glycols. They are prepared by the ring-opening polymerization of tetrahydrofuran, and contain the repeating unit.

in the polymer backbone. Termination of the polymer chains is by hydroxyl groups.

Also especially desirable are the polyoxyethylene polyols HO$-$(CH$_2$CH$_2-$O$-$)$_x$H, because of their tolerance for and compatibility with aqueous solutions of enzymes.

The polyester polyols which may be employed as precursors are most readily prepared by condensation polymerization of a polyol with a polybasic acid. The polyol and acid reactants are used in such proportions that essentially all the acid groups are esterified and the resulting chains of ester units is terminated by hydroxyl groups. Representative examples of polybasic acids for producing these polymers are oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethylglutaric acid, α, β-diethylsuccinic acid, o-phthalic acid, isophthalic acid, terephthalic acid, hemimellitic acid, trimellitic acid, trimesic acid, mellophanic acid, prehnitic acid, pyromellitic acid, citric acid, benzenepentacarbosylic acid, 1,4-cyclohexane dicarboxylic acid, diglycollic acid, thiodiglycollic acid, dimerized oleic acid, dimerized linoleic acid, and the like. Representative examples of polyols for forming these polymers include ethylene glycol, 1,3-propylene glycol, 1,2-propylene glycol, 1,4-butylene glycol, 1,3-butylene glycol, 1,2-butylene glycol, butene-1,4 diol, 1,5-pentane diol, 1,4-pentane diol, 1,3-pentane diol, 1,6-hexane diol, hexene-1,6-diol, 1,7-heptane diol, diethylene glycol, glycerine, trimethylol propane, 1,3,6-hexanetriol, trimethanolamine, pentaerythritol, sorbitol, and any of the other polyols listed hereinabove in connection with the preparation of polyether polyols. The water soluble (polyethylene glycol based) polyurethanes represent a preferred class for this process.

On being intimately contacted with the aqueous enzyme dispersion, the isocyanate-capped polyurethane becomes chemically very active. Some of its free isocyanate groups react with the amine groups of the enzyme, and some react with water to give carbon dioxide and to form amine groups on the polyurethane molecule. These latter amine groups react with free isocyanate groups on neighboring polyurethane molecules, and this reaction (forming a urea linkage) will cause further growth of the polyurethane and will also introduce cross links between the polyurethane molecules. This further preliminary growth and cross linking is essential for the formation of a good polyurethane foam. We have found that this growth must occur during contact with the enzyme for binding of the enzyme to take place. If the growth and foaming reactions are permitted to go to completion in the absence of the enzyme, the enzyme will not bind to the finished foamed polyurethane.

Other additives such as crosslinking agents (polyamines, polythiols, polyacids) or antioxidants, fillers, etc. may also be present during foaming.

It is, of course, the release of the carbon dioxide that provides gas for foam formation. And as we have explained, it is the absence of a water-immiscible solvent (such as required by Stanley) that makes the reaction mix sufficiently viscous to retain the carbon dioxide as bubbles of foam.

Reusable nature of bound enzyme:

The bound enzyme product of this invention can be used in either a broth or continuous process. In either case it can be re-used indefinitely. E.g., bound enzyme was used in a batch process; after reaction was complete it was removed by filtering, centrifuging or just lifting out if it was in a single piece. The bound enzyme was then placed in another substrate reactor and was still fully active. Bound urease was placed in column and substrate passed through in continuous fashion. The enzyme was still active after six months of operation.

The following examples illustrate without limiting the invention.

EXAMPLE 1

Ethylene glycol (100 gm) and toluene diisocyanate (282 gm) were mixed in a constant temperature bath at 65° C. After the material becomes water clear, it was cooled to 4° C. and 100 ml of a fermentation broth containing cellulase activity was added with constant stirring at 4° C. After polyurethane foam formation was complete, about 15 minutes, the foam was washed with water and assayed for cellulase activity using carboxymethyl cellulose as substrate and found to be active.

EXAMPLE 2

The procedure of Example 1 was followed except that 100 ml of a 10% solution of pectinase in a 0.1 M phosphate buffer of pH of 5 was used instead of broth. After polyurethane foam formation was complete, the foam was washed with water, cut into small pieces, and placed into a column. Freshly prepared apple juice containing 0.1% sodium benzoate was passed through the column at a rate of 1 liter per hour. The column clarified the apple juice as it passed through it, and the product had no changed flavor characteristics.

EXAMPLE 3

A prepolymer was prepared in which 690 g. polyethylene glycol of molecular weight 1000 containing 310 g. pentaerythritol was reacted with 1830 g. of toluene diisocyanate. (Pentaerythritol contributes cross-linking and improves heat-stability.) The polyurethane prepolymer (8.0 gm) was cooled to 4° C. and then added to a 4° C. solution containing 1.0 gm trypsin dissolved in 5.0 ml of a 0.1 M trishydroxyethylaminoethane buffer of pH 8.0 containing 0.01 M calcium chloride. The mixture was stirred and maintained at 4° C. until it began to foam. After polyurethane foam formation was complete (about 15 minutes) the foam was washed in the above buffer-salt solution until the wash water showed no ultraviolet absorption. The washed polyurethane foam was assayed for trypsin activity by placing it in a buffered solution of 1% casein and measuring the increase of trichloracetic acid soluble absorption at 280 m$\mu$ as a function of time, and found to be active.

EXAMPLE 4

The procedure of Example 3 was followed except that a 20% urease solution was used instead of trypsin. Final washed polyurethane foam was placed into a column and a 0.1 M urea solution was passed through. After 4 months of continuous operation, the column was still active in the hydrolysis of urea to ammonia and carbon dioxide as measured by pH rise of effluent solution.

EXAMPLE 5

Propylene glycol (10 g) was added to toluene diisocyanate (10 g) in a metal dish. The dish was placed on a hot plate and the compounds stirred until a homogeneous mixture was obtained, care being taken that no boiling or vaporization of the liquid took place. The solution was removed from the heat and 1.0 ml of a solution containing 10% amyloglucosidase in 0.1 M phosphate buffer, pH 7.0, was added. The mixture was stirred rapidly until it became viscous (approximately 10 to 15 minutes). The material was then allowed to stand overnight at room temperature to finish polyurethane foam formation. The product was then submerged for 12 hours in water to remove any excess NCO groups. The resultant product was a crystalline polyurethane foam which was washed and shown to be active in hydrolyzing a 1% starch solution.

EXAMPLE 6

An elastomeric foam which contained bound amyloglucosidase was prepared in the manner of Example 5, except the amount of propylene glycol used was 20 g.

EXAMPLE 7

A commercial polyisocyanate containing 9.5% free NCO and having 7 repeating butoxy groups (10 g) was added to 1.0 ml of an enzyme solution (same as Example 5).

The mixture was stirred until a viscous foam was obtained (5 to 10 minutes). The material was then allowed to stand overnight at room temperature to finish foam formation. The product was submerged for 12 hours in water to remove excess NCO groups. The resultant foam bound enzyme was washed and was enzymatically active.

EXAMPLES 8 AND 9

Example 3 was repeated except that the pentaerythritol was consecutively replaced first by glycerol (Example 8) and second by trimethylol propane (Example 9). Similar results were obtained.

EXAMPLE 10

Polyethylene glycol of molecular weight 1000 was dried by heating for two hours at 110° C. under nitrogen at reduced pressure. Toluene diisocyanate (1.48 moles per mole of hydroxyl) was added gradually with stirring while the temperature was maintained at 30° C. in a cooling bath. After addition was complete, the temperature was raised to 60° until reaction was complete (about two hours). This prepolymer (10 gm) was added to a solution of 10% lactase enzyme in a 4% lactose solution (10 gm). The reactants were stirred until foaming began. The resultant foam was washed in water to remove the lactose, and then placed in a lactose solution and glucose was liberated.

EXAMPLE 11

A prepolymer was prepared in which polyethylene glycol of molecular weight 1000 containing 33% (wt/wt) glycerol was reacted with 2.63 meq. of toluene diisocyanate. The prepolymer was added to an equal weight of the supernate after centrifugation of a fermentation broth of a glucose isomerase producing organism whose cells had been previously disrupted by sonication (ultra-sonic vibrations). The resultant foam was washed thoroughly and was placed in a 30% glucose solution containing 0.2 M MgSO$_4$. After stirring for 24 hours at 70°, the resulting solution contained approximately 15% glucose and 15% fructose. In this example, a triol (glycerol) was used to produce crosslinking in a foam to add to the heat stability of the foam carrier.

EXAMPLE 12

Conversion of penicillin G to 6-aminopenicillanic acid

Penicillin amidase was extracted from Escherichia coli ATCC 9637 grown on phenylacetic acid and corn steep liquor, by ammonium sulphate precipitation (D. A. Self, G. Kay and M. D. Lilly, *BIOTECHNOLOGY AND BIOENGINEERING*, Vol. XI, pg. 337–348 [1969]. A water solution of the enzyme (40 mg/ml) was added to an equal weight of the prepolymer described in Example 11. The temperature of the reaction mixture was maintained at 25° or below with stirring. After foam formation was complete (about 10 minutes), the resultant foam was cut into small pieces (8 mm$^3$) and washed thoroughly in water. The washed foam was placed into a 10% solution of penicillin G and maintained at a pH of 8.0 and 37° C. Aliquots were removed with time and assayed for 6-aminopenicillanic acid using p-dimethylaminobenzaldehyde (Joseph Bomstein and William G. Evans, *ANALYTICAL CHEMISTRY*, Vol. 37, pg. 576–578 [1965]). After all the penicillin had been converted, the foam was removed. The foam was washed with water and placed into another sample of substrate. The time required for complete conversion of the second sample was equal to the first, showing the enzyme was still present in the foam.

What is claimed is:

1. A foamed polyurethane product containing an enzyme internally bound thereto prepared by the method which includes contacting, prior to a subsequent foaming step, an isocyanate-capped polyurethane with an aqueous dispersion of an enzyme, under foam-forming conditions, whereby the polyurethane foams and the enzyme becomes integrally bound to the thus formed polyurethane foam.

2. The product of claim 1 in which the polyurethane is formd by contacting an isocyanate-capped polyurethane with an aqueous dispersion of an enzyme, under foam-forming conditions, whereby the polyurethane foams and the enzyme becomes bound to the thus formed polyurethane foam, the isocyanate-capped polyurethane being the reaction product of toluene diisocyanate and a polyhydroxy compound selected from the group consisting of polyoxybutylene polyol polymer, ethylene glycoldiethylene glycol, polyoxyethylene polyol polymer, pentaerythritol, glycerol, trimethylol propane and polyoxypropylene polyol polymer.

3. The product according to claim 1 in which the enzyme is a member of a group consisting of urease, cellulase, pectinase, papain, bromelain, chymotrypsin, trypsin, ficin, lysozyme, lactose, penicillin amidase, and glucose isomerase.

* * * * *

UNITED STATES PATENT AND TRADEMARK OFFICE
CERTIFICATE OF CORRECTION

PATENT NO. : 4 342 834
DATED : August 3, 1982
INVENTOR(S) : Wood, Hartdegen, Hahn It is certified that error appears in the above-identified patent and that said Letters Patent are hereby corrected as shown below:

Claim 1, line 2, change "internally" to --integrally--.

Signed and Sealed this

Fifth Day of October 1982

[SEAL]

Attest:

GERALD J. MOSSINGHOFF

Attesting Officer     Commissioner of Patents and Trademarks